United States Patent [19]

Levinson

[11] Patent Number: 5,235,973
[45] Date of Patent: Aug. 17, 1993

[54] TRACHEAL TUBE CUFF INFLATION CONTROL AND MONITORING SYSTEM

[76] Inventor: Gary Levinson, 22 Beaumont Dr., Mason City, Iowa 50401

[21] Appl. No.: 701,450

[22] Filed: May 15, 1991

[51] Int. Cl.$^5$ ............................................. A61M 16/00
[52] U.S. Cl. ........................... 128/207.15; 128/207.14; 128/205.23
[58] Field of Search ...................... 128/200.26, 202.22, 128/205.23, 207.14, 207.15, 207.16, 715, 773

[56] References Cited

U.S. PATENT DOCUMENTS

| | | | |
|---|---|---|---|
| 3,407,817 | 10/1968 | Galleher | 128/351 |
| 3,481,339 | 12/1969 | Puig | 128/351 |
| 3,504,676 | 4/1970 | Lomholt | 128/207.15 |
| 3,529,596 | 9/1970 | Garner | 128/145.6 |
| 3,543,751 | 12/1970 | Sheffer | 128/207.16 |
| 3,633,586 | 1/1972 | Sheridan | 128/351 |
| 3,642,005 | 2/1972 | McGinnis | 125/351 |
| 3,682,166 | 8/1972 | Jacobs | 128/145.8 |
| 3,707,151 | 12/1972 | Jackson | 128/351 |
| 3,731,691 | 5/1973 | Chen | 128/351 |
| 3,731,692 | 5/1973 | Goodyear | 128/351 |
| 3,794,026 | 2/1974 | Jacobs | 128/207.15 |
| 3,794,043 | 2/1974 | McGinnis | 128/349 |
| 3,848,605 | 11/1974 | Harautuneian et al. | 128/351 |
| 3,931,822 | 1/1976 | Marici | 128/207.15 |
| 3,985,141 | 10/1976 | Stanley et al. | 128/351 |
| 4,016,885 | 4/1977 | Bruner | 128/349 |
| 4,020,849 | 5/1977 | Jackson | 128/351 |
| 4,090,518 | 5/1978 | Elam | 128/349 B |
| 4,116,201 | 9/1978 | Shah | 128/207.15 |
| 4,119,101 | 10/1978 | Igich | 128/351 |
| 4,134,407 | 1/1979 | Elam | 128/207.15 |
| 4,147,170 | 4/1979 | Taylor | 128/349 BV |
| 4,159,722 | 7/1979 | Walker | 128/207.15 |
| 4,178,940 | 12/1979 | Au | 128/207.15 |
| 4,224,939 | 9/1980 | Lang | 128/205.13 |
| 4,248,222 | 2/1981 | Jaeger et al. | 128/207.15 |
| 4,256,099 | 3/1981 | Dryden | 128/200.26 |
| 4,270,530 | 6/1981 | Baum et al. | 128/204.25 |
| 4,280,492 | 7/1981 | Latham | 128/207.16 |
| 4,285,340 | 8/1981 | Gezari et al. | 128/205.24 |
| 4,316,458 | 2/1982 | Hammerton-Fraser | 128/205.24 |
| 4,383,534 | 5/1983 | Peters | 128/671 |
| 4,471,775 | 9/1984 | Clair et al. | 128/205.24 |
| 4,488,548 | 12/1984 | Agdanowski | 128/204.25 |
| 4,501,273 | 2/1985 | McGinnis | 128/207.15 |
| 4,519,388 | 5/1985 | Schwanbom et al. | 128/204.25 |
| 4,526,196 | 7/1985 | Pistillo | 137/557 |
| 4,565,194 | 1/1986 | Weerda et al. | 128/204.23 |
| 4,573,462 | 3/1986 | Baum | 128/204.25 |
| 4,583,917 | 4/1986 | Shah | 128/207.15 |
| 4,617,015 | 10/1986 | Foltz | 604/100 |
| 4,644,947 | 2/1987 | Whitwan et al. | 128/207.16 |
| 4,646,733 | 3/1987 | Stroh et al. | 128/207.16 |
| 4,649,914 | 3/1987 | Kowaleski | 128/207.15 |
| 4,825,862 | 5/1989 | Sato et al. | 128/207.16 |
| 4,924,862 | 5/1990 | Levinson | 128/202.22 |
| 4,967,759 | 11/1990 | Teves | 128/715 |

Primary Examiner—Edgar S. Burr
Assistant Examiner—Aaron J. Lewis
Attorney, Agent, or Firm—Fish & Richardson

[57] ABSTRACT

A tracheal tube is equipped with two air lines to the inflatable cuff, one for monitoring cuff pressure and another of larger diameter for inflating the cuff. Intracuff pressure monitored via the smaller diameter line is continuously displayed. A cuff pressure control system allows independent adjustment of cuff pressure via the larger diameter line from high pressure during inspiration to low pressure during expiration. The switchover point is determined by a detecting pressure monitor in the mechanical ventilator inspiration line. The circuit also adjusts automatically to changes in the baseline expiration pressure. The output of a bidirectional mass flow sensor tracks airflow in the cuff inflation line and is integrated to indicate volume. Volume into the cuff is then compared to volume out of the cuff to detect cuff leakage.

5 Claims, 4 Drawing Sheets

FIG. 3B

TRACHEAL TUBE CUFF INFLATION CONTROL AND MONITORING SYSTEM

CROSS REFERENCE TO RELATED APPLICATIONS

The subject matter of this application is related to that of U.S. Pat. No. 4,924,862 issued May 15, 1990 to Gary Levinson, entitled "Pressure Controller and Leak Detector for Tracheal Tube Cuff", which is incorporated herein by reference in its entirety.

BACKGROUND OF THE INVENTION

The invention relates to the controlled inflation of balloon cuffs which surround the end of tracheal tubes used in respiratory medicine. Tracheal tubes include both tracheostomy and endotracheal tubes. An endotracheal tube is one which can quickly be inserted through the mouth or nose into the trachea, while a tracheostomy tube must be inserted through a surgical opening in the neck. However for the purposes of this invention, they may be viewed as the same, and will therefore herein be referred to collectively as tracheal tubes, unless otherwise stated.

Tracheal tubes may be inserted for a variety of reasons, including, the need for mechanical ventilation, bypass of an obstruction, removal of secretions, easier ventilation due to less dead space. In most circumstances, it is necessary to seal the outside of the tracheal tube to the inner tracheal lining, i.e., the tracheal mucosa. During mechanical ventilation, this is particularly true, since a closed circuit is necessary for a ventilator to force a given volume of air or oxygen under pressure into a patient's lungs. When a patient is not being mechanically ventilated, a seal may or may not be required. In this situation, the need for a seal will generally depend on whether or not there is a risk of aspiration. In the case of an endotracheal tube, this risk is always present, while with a tracheostomy tube, this risk is often present. Therefore, most patients require a seal either to prevent aspiration or to create a closed circuit for mechanical ventilation. Because of the pressurization of the system, a tighter seal is necessary during mechanical ventilation than is necessary to prevent aspiration in the absence of mechanical ventilation.

It is well known that over-pressurization of the tracheal cuff can cause significant tracheal damage including hemorrhage, ulcers, perforation, and strictures. It is generally accepted that the main cause of this damage is occlusion of blood vessels leading to loss of blood flow with resultant necrosis of the tracheal lining. Experience has shown that an intra cuff pressure of less than 25 cm $H_2O$ is associated with significantly fewer complications. This is consistent with experimental data suggesting that the capillary perfusion pressure in the tracheal mucosa is in the range of 30–40 cm $H_2O$. Thus, a cuff pressure of 25 cm $H_2O$ would still allow some blood flow. However, the numbers noted above are not absolute. Damage is occasionally seen with cuff pressures of 25 cm $H_2O$ because perfusion pressures may be lower than expected due, for example, to low blood pressure. Therefore, the best approach is to use the lowest cuff pressure consistent with an adequate ventilation seal and the prevention of aspiration.

Tracheal cuffs are frequently positional, that is, as the patient moves, the balloon moves into tighter and looser positions within the trachea. This causes the pressure in the cuff to increase and decrease respectively. The result is either too much pressure on the mucosa or a pressure leak. The problem of tracheal tube movement is not just a theoretical one. The phrases "positional tube" or "positional cuff" are ones frequently heard in practice to report a condition in which, after proper inflation of a cuff, movement of the patient causes excessive, often audible leakage of the ventilator volume around the cuff. In this case, the patient's lungs fail to receive the prescribed volume. In addition, the loss of a seal between the cuff and trachea allows aspiration to occur.

A further cause of loss of a seal with resultant aspiration and leakage of ventilator volume is a leak in the cuff itself or in the cuff inflation line.

Problems relating to tracheal cuff pressure control and monitoring have been the subject of numerous articles in the medical literature over the years. To summarize, the problem is to achieve cuff pressures high enough to prevent aspiration and loss of ventilator volume without causing any damage to the tracheal mucosa. Solving this problem has been particularly difficult because of the wide range of clinical conditions in which the cuff system is required to function. For example, in the setting of an irregular trachea, stiff lungs requiring high pressures to ventilate, and low blood pressure, the minimum cuff pressure needed to prevent loss of ventilator volume might cause mucosal damage.

Over the years numerous tracheal tubes and cuff pressure controllers have been designed and patented for the purpose of improved cuff pressure control. To date no completely satisfactory system has been designed which solves the problems of tracheal cuff control and monitoring.

The tracheal tubes have one thing in common, namely, they all have one inflation line communicating with the cuff for the purpose of inflating it. Several tracheal tubes have been designed with two cuffs. However, each cuff has a single inflation line. There are two major problems with the existing tracheal tubes. In the first place, existing inflation lines are of a small diameter ranging from 0.015"–0.030". While this diameter is satisfactory for slowly inflating a cuff, it is inadequate for rapid, synchronous inflation and deflation of a tracheal cuff. Because of the small diameter, the high resistance to flow does not allow rapid enough inflation and deflation of the tracheal cuff at the low pressures which are used for tracheal cuff inflation. The second problem is that it is not possible to synchronously inflate and deflate a cuff, and continuously monitor cuff pressure through a single inflation lumen. This is because the resistance of the inflation lumen causes significant pressure differential between the external applied pressure and the actual intracuff pressure. The greater the flow through the inflation lumen, the greater the difference between applied pressure and actual pressure in the cuff.

In addition to numerous tracheal tube designs, a number of tracheal cuff controllers have been designed, for the purpose of more accurately applying pressure to the tracheal tube cuff. These systems have generally overpressurized cuffs for different reasons. In most cases they have not allowed continuous bidirectional cuff pressure control. In other cases, the application of PEEP was communicated to the cuff pressure, while in other cases too much baseline pressure was applied to the cuff.

In my previous patent (U.S. Pat. No. 4,924,862) I describe a "Pressure Controller and Leak Detector for Tracheal Tube Cuff". That design solved many of the problems of tracheal cuff control. I herein describe a new tracheal tube to be used in association with a significantly improved Pressure Controller and Leak Detector.

SUMMARY OF THE INVENTION

A general feature of the invention is a tracheal tube with two separate and distinct tubules entering the cuff. The first tubule is a cuff monitoring line of standard diameter, while the second tubule is a cuff inflation line of a significantly larger diameter than is generally found in tracheal tubes.

Another general feature of the invention is a bidirectional continuous inflation control system for a tracheal tube cuff including a pressure relief valve having an inlet, an outlet and an exhaust port urged toward the closed condition, and a cuff inflation line connecting the inlet and outlet of the relief valve in series between a source of pressurized gas and the cuff. The cuff inflation line connects to the cuff by way of the larger diameter tubule entering the cuff of said tracheal tube.

Two pressure relief valves are preferred: a low pressure valve in series with a high pressure valve in the cuff inflation line. Each valve has an inlet and an outlet and a valved exhaust port urged toward the closed condition, the high pressure valve requiring higher pressure in the cuff inflation line to open the exhaust port than the low pressure valve. The inlets and outlets of both valves are connected in series in the cuff inflation line. This arrangement offers the capability of adjusting the pressure in the cuff according to either of two limits while continuously maintaining the ability to supply additional volume to the cuff. Thus, during inhalation, the cuff pressure can be regulated by the setting of the higher pressure relief valve by, in effect, disabling the low pressure relief valve.

A further general feature of the invention is the continuous monitoring and display of intra-cuff pressure. This is achieved by the connection of a pressure transducer to the first, smaller, or monitoring tubule which enters the cuff. In the preferred embodiment cuff pressure would be instantaneously and continuously displayed such as on a CRT or LED Bar Graph.

When the tracheal tube is connected to a mechanical ventilator, another feature of the invention is brought into play, in which the exhaust port of the aforementioned low pressure relief valve, which is in series with the high pressure relief valve, is blocked. In the preferred embodiments of the invention, a pressure transducer continuously monitors the ventilator pressure in the inspiratory tubing and when a specific pressure threshold is reached a solenoid is actuated which blocks the exhaust port of the low pressure relief valve.

In the preferred embodiment, the low and high pressure valves are magnetic PEEP type valves as hereinafter described.

A further feature of the invention is to monitor cuff leaks by means of a bidirectional flow detector which produces an electrical output signal indicative of the magnitude and direction of airflow in the cuff inflation line. In the preferred embodiment, flow is integrated to indicate volume. Volume into the cuff is then compared to volume out of the cuff to determine if there is a cuff leak. An alarm circuit signals a leak if volume into the cuff exceeds volume out of the cuff. In the preferred embodiment, flow is measured by means of a mass flow sensor.

The features of the invention provide continuous instantaneous monitoring of cuff pressure, automatic bidirectional pressure control of the tracheal tube cuff during both respiratory phases, as well as cuff leak protection.

Other advantages and features will become apparent from the following description of the preferred embodiments and from the claims.

BRIEF DESCRIPTION OF THE DRAWINGS

The drawings are briefly described as follows.

DESCRIPTION OF PREFERRED EMBODIMENTS

Figures 1, 2A, 2B, 4:
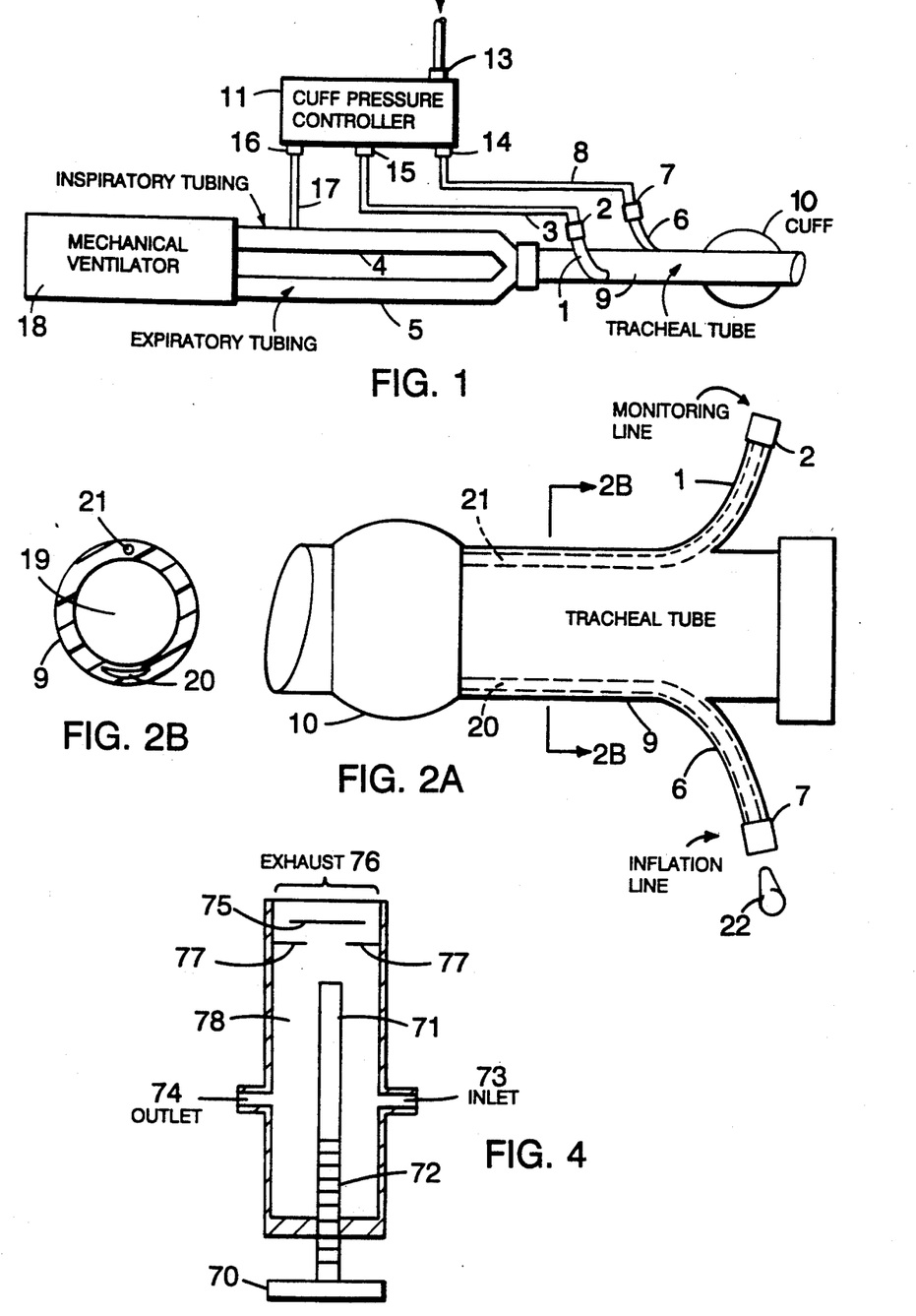
FIG. 1 is a block diagram showing the external connections between the tracheal tube, the cuff pressure controller, and a mechanical ventilator, according to the invention.
FIG. 2A is a diagrammatic side view of the tracheal tube of FIG. 1.
FIG. 2B is a diagrammatic cross-sectional view of the tracheal tube taken along lines A—A of FIG. 2A.
FIG. 4 is a sectional view of a PEEP valve of the type employed in the controller of FIG. 3.

FIG. 1 is a schematic diagram showing the external connections between the tracheal tube 9, the cuff pressure controller-monitor 11 (hereinafter referred to as the controller), and a mechanical ventilator 18. A source gas is supplied through fitting 13. Since the pressure standard in hospitals is 50 psi, the controller 11 has been designed to accept source gas of that pressure. Fitting 14 is the cuff inflation line and connects via external tubing 8 to fitting 7 of tracheal tube 9. This line is for the purpose of synchronously and rapidly inflating and deflating the tracheal cuff 10 mounted on the distal end of tracheal tube 9. Fitting 15 of controller 11 connects via external tubing 3 to fitting 2 of tracheal tube 9. This line is for the purpose of continuously and instantaneously monitoring the actual pressure in tracheal cuff 10. Fitting 16 of controller 11 connects via external tubing 17 to inspiratory tubing 4 of mechanical ventilator 18. This connection allows the controller 11 to continuously monitor the pressure in the inspiratory tubing 4 which connects via trach tube 9 to the patient's airway. This continuous monitoring allows the controller 11 to synchronize itself with the phases of ventilation.

FIG. 2 and 2B illustrate the tracheal tube 9. The tracheal tube is fitted with two separate and distinct tubules entering the cuff 10. Each tubule consists of both a section which is formed within the wall of the tracheal tube and a section which is external to the main body of the tracheal tube 9. As shown in FIG. 2A, fitting 7 will receive the inflation line coming from the controller 11. This fitting is in gaseous communication with tubule 6, which is in gaseous communication with tubule 20. Tubule 20 represents the portion of the inflation line which is formed within the wall of the tracheal tube 9. To allow rapid inflation and deflation of the tracheal cuff, the entire inflation line tubule preferably has a cross-sectional area of approximately six times that of the standard tracheal tube. In the cylindrical state this would require a diameter of approximately 2½ times that of the standard tubule or a diameter of 0.060–0.080". This is not a problem for tubule 6, which is external to the wall of the tracheal tube 9. However, a cylindrical diameter of 0.060–0.080" within the wall of tracheal tube 9 would not be possible, because that is the approximate wall thickness of the tracheal tube itself. Therefore, as noted in FIG. 2B, tubule 20 would have to assume either an oval or crescent shape in cross-section in order to achieve the required cross-sectional area of about six times the standard tubule.

As shown in FIG. 2A, fitting 2 will receive the monitoring line from the controller 11. This fitting is in gaseous communication with external tubule 1, tubule 21, and cuff 10. Because there is insignificant net flow in the monitoring line, there is no requirement for this to be of an increased cross-sectional area. Therefore, this line may be of the standard diameter. Section 21 is formed within the wall of the tracheal tube 9, while section 1 is external to the body of the tracheal tube 9. In the preferred embodiment, fitting 2 would be fashioned with a spring-loaded plug (not shown) as currently exists in most tracheal tubes in use today, such as the endotracheal tube made by Portex, catalog No. 197080. These plugs prevent flow in and out of the cuff. The fitting 2 contains a female intravenous tubing taper. When a male intravenous tubing taper is formed into this fitting, the plug is unseated, so that bidirectional flow can occur. This design is typical of tracheal tubes currently in use. However, fitting 7, which would also have a female intravenous tubing taper, would contain no spring-loaded plug. This is because a spring-loaded plug would cause restriction to rapid flow. Instead, the open end of fitting 7 would be fitted with a small removable male plug 22 (FIG. 2A) which would keep this fitting closed. In that way, this tracheal tube can be used without the controller 11 (FIG. 1), as if it were a single line tracheal tube such as is commonly in use today. In that case the cuff would be manually inflated through monitoring line 1 and 21. To connect the tracheal tube 9 to the controller 11, one would merely have to remove the plug 22 from fitting 7 and connect the inflation line 8 as indicated in FIG. 1.

Figure 3:
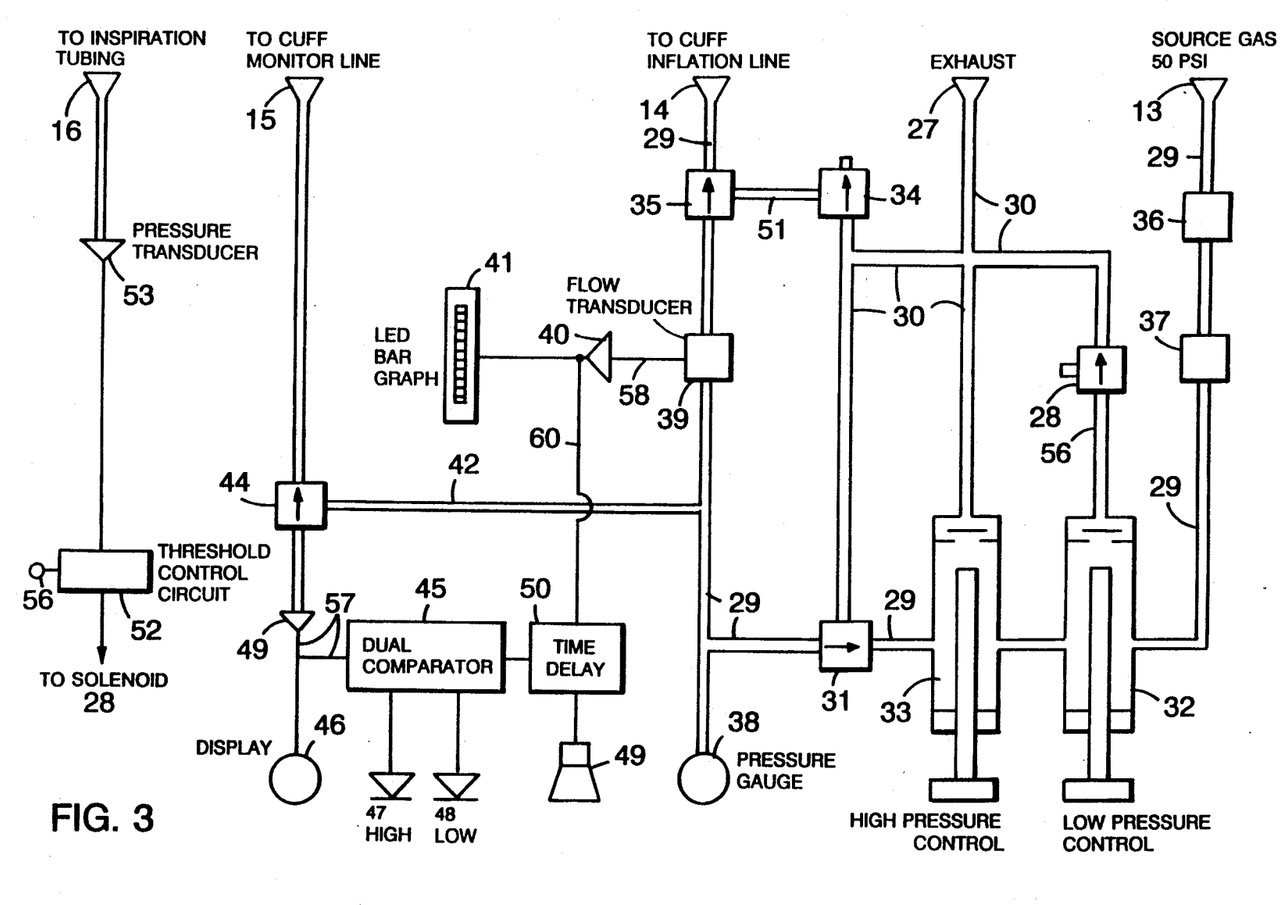
FIG. 3 is a schematic diagram of the internal pneumatic and electrical design of the cuff pressure controller of FIG. 1.

FIG. 3 is a schematic diagram of the internal pneumatic and electrical design of the controller 11 seen in FIG. 1. Along the top of the diagram are seen the four external connections noted in FIG. 1, plus a fifth tube which is the exhaust port (not shown in FIG. 1). A 50 psi source gas is connected to fitting 13. The gas flows within tube 29 through filter 36, preferably 43 microns, and restrictor 37. In line filters and restrictors are available from Air Logic, Inc. Restrictor 37, preferably 0.007 to 0.010 inch, limits the maximum flow into the system. A flow of 1-2 liters per minute is most desirable. Flow then continues within tube 29 through pressure controllers 32 and 33, through solenoid 31 shown in its at-rest position, through flow transducer 39, such as AWM2300V from the Microwswitch Division of Honeywell, Inc., through solenoid 35 shown in its at rest position, out fitting 14. As indicated in FIG. 1, fitting 14 is connected to the inflation line tubule by way of external tube 8 and fitting 7. Therefore, in FIG. 3, tube 29 represents the main path of supply gas in and out of the cuff.

The operation of pressure controllers 32 and 33 will now be discussed. Positive end expiratory pressure (PEEP) valves are normally used to apply PEEP to a patient's lungs in order to improve oxygenation. They provide back pressure or resistance to exhalation so as to maintain therapeutic pressure on the lungs. Thus it is not uncommon to find a PEEP valve with just an inlet and an exhaust port in the expiratory tubing (5 in FIG. 1).

As shown in FIG. 3, a pair of modified PEEP type valves, 32 and 33, are employed in a different way in the controller 11. In essence, these valves are adjustable pressure relief valves. They maintain their pressure by actually releasing or bleeding off volume when the preset pressure is exceeded. Unlike the conventional usage in the expiratory line, here the PEEP type valves are connected with inlets and outlets in series with the cuff inflation line 29. Because of the bidirectional nature of this control system, the pressures will always end up at exactly the preset point, whether the cuff pressure begins above or below that point. The PEEP valves thus can instantaneously supply either extra volume to, or accept extra volume from, the cuff. Either magnetic or spring-loaded PEEP valves may be used, though the design herein described uses magnetic ones, e.g. of the type manufactured by Instrumentation Industries, Inc., of Bethel Park, Pa.

FIG. 4 shows the functional design of a magnetic PEEP valve as applied to the controller 11. Gas enters port 73 at a rate of 1-2 liters per minute and at a high pressure. Knob 70 turns magnet 71 via thread 72 closer to or further from the diaphragm 75. Diaphragm 75 is usually ferrous metal embedded in rubber. The closer magnet 71 is to the diaphragm 75, the tighter the diaphragm 75 is pulled against orifice flange 77, and the greater the pressure needed to unseat the diaphragm 75. When the pressure in chamber 78 reaches the preset point determined by the position of magnet 71, the excess pressure unseats diaphragm 75 and gas exhausts out port 76. Port 74 ultimately connects to the tracheal cuff 10. Once the system is pressurized, there is usually no net flow out port 74. Therefore, the pressure in chamber 78 is equal to that of the cuff 10. If the cuff pressure falls, chamber 78 will supply just enough volume to port 74 from inlet 73 to equalize the pressure in the cuff to that of chamber 78. If the cuff pressure rises, chamber 78 will accept extra volume from port 74 and exhaust it out port 76 until the pressure in the cuff is equalized to that of chamber 78.

Referring back to FIG. 3, low pressure control 32 has a range of 0-35 cm $H_2O$. Low pressure control 32 is always adjusted to a lower pressure than high pressure control 33. Therefore, under normal circumstances, low pressure control 32 determines system pressure, since volume is exhausted out the exhaust port of low pressure control. All of the exhaust gas exiting low pressure controller 32 enters line 56, travels through solenoid 28 shown in its atrest condition, enters exhaust tubing 30 and exhausts out fitting 27 to atmosphere. When solenoid 28 is actuated, tube 56 is closed essentially blocking the exhaust port of low pressure control 32. This essentially renders low pressure control 32 non-functional and the source gas merely passes through it and enters high pressure control 33. System pressure then rises quickly, above that set by low pressure control 32, until it reaches a pressure high enough to unseat the exhaust diaphragm of high pressure control 33. This pressure is determined by the position of the magnet as described above under the discussion of the PEEP valve shown in FIG. 4. The setting of high pressure control 33 then determines the system and therefore the cuff pressure. Exhaust gas from high pressure controller 33 enters the exhaust tube 30 and exhausts out of fitting 27 to atmosphere. When solenoid 28 is again returned to its at rest position, low pressure controller 32 becomes functional and again determines system, and therefore cuff pressure. The controller is designed so that low pressure control 32 determines cuff pressure during expiration while high pressure control 33 determines cuff pressure during inspiration. Pressure gauge 38 is a mechanical pressure gauge and is used to set both pressure control points.

External fitting 16 connects to the inspiratory tubing of the ventilator circuit by way of external tubing 17 of FIG. 1. Therefore, pressure transducer 53 continuously monitors the pressure within the inspiratory tubing which connects to the patient's airway. The electrical output of pressure transducer 53 is connected to the threshold control circuit 52. The output of threshold control circuit 52 connects to solenoid 28. Threshold control circuit 52 determines the inspiratory tubing (4 of FIG. 1) pressure, at which solenoid 28 opens and closes. This threshold point is adjustable by the user via potentiometer 56, which is mounted on the front panel of the controller 11. Therefore, the user can determine the point in the inspiratory cycle of the ventilator (18 of FIG. 1) at which the cuff pressure is changed from low pressure control to high pressure control. The threshold control circuit is designed such that positive end expiratory pressure applied to the inspiratory tubing 4 via the mechanical ventilator 18 will not affect the set point for the switching of solenoid 28. This is because the threshold control circuit considers the baseline pressure in the inspiratory tubing 4 to be zero, whether that pressure is actually zero or some positive pressure above zero. A subtraction circuit in the threshold control circuit subtracts the electrical output of the transducer measured at baseline pressure from the electrical output of the transducer continuously. In that way, the application of PEEP and the adjustment of PEEP by the mechanical ventilator will not affect the previous setting of the threshold control circuit 52.

Figure 3A:
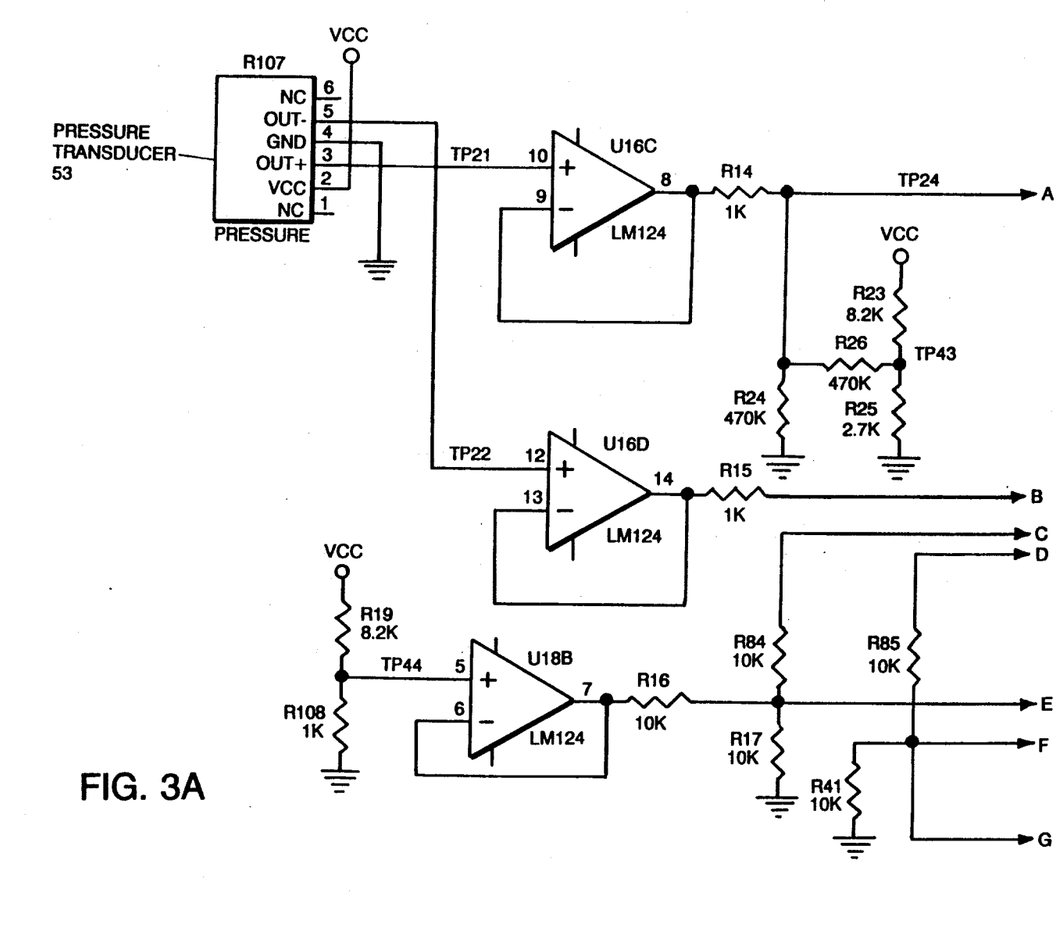

A preferred circuit implementation of the threshold control circuit 52 is set forth in FIG. 3A. The positive and negative outputs of transducer 53 are fed via respective operational amplifiers U16C and D to differential amplifier U18A, a voltage offset being summed with the positive input signal by a voltage divider resistor network as shown. The output of amplifier U18A is the instantaneous measurement output or "actual output" corresponding to the sensed pressure. This actual output is fed to the positive input to differential amplifier U17B, summed with the output of voltage offset follower U18B and associated circuitry. The negative input to differential amplifier U17B is provided by a diode/capacitor peak follower circuit involving operational amplifiers U17A and U18D. Diode D6 causes capacitor C2 to fall back to the baseline value quickly after each cycle to keep track of the most recent low-point of the actual sensed output. Thus the output of the differential amplifier U17B is the difference between the instantaneous sensed pressure and the current baseline pressure experienced during exhalation. The output of the differential amplifier U17B is threshold detected by means of comparator U18C whose reference voltage is set by potentiometer 56, as shown.

Referring back to FIG. 1, fitting 15 is connected to the cuff monitor line by way of external tube 3. By that means, pressure transducer 49 continuously monitors cuff pressure when solenoid 44 is in its at-rest position, as shown in FIG. 3. The electrical output of pressure transducer 49 is conducted over wire 57 to both a dual comparator 45 and an instantaneous display system 46. In the preferred embodiment, the display system would be a CRT so that real time pressures can be seen. However, an LED bar graph can be utilized satisfactorily. The key factor here is the need to monitor instantaneous and continuous changes. Therefore, a mechanical pressure gauge would not have a quick enough response time. The pressure display 46, in conjunction with observations of the patient, is used to help adjust the three determinants of cuff pressure, namely, the low pressure controller 32, the high pressure controller 33, and the setting of the threshold control circuit 52 via potentiometer 56. The dual comparator 45 monitors the output voltage in wire 57, and therefore the pressure in the cuff. If either a preset high or low pressure limit is exceeded, either LED 47 or LED 48 lights respectively. The output of dual comparator 45 also enters a time delay circuit 50 which is set for a 10-15 second delay. If the pressure limits are exceeded for a period greater than that time, tweeter 49 sounds, indicating too high or too low a pressure. If, on the other hand, the out of range pressure normalizes in less than 10-15 seconds, the time delay circuit resets itself and the tweeter does not sound. Therefore, the alarm circuit is designed such that the LED's continuously and instantaneously indicate whether the preset limits are exceeded, while the tweeter sounds only if an out of range pressure is detected for a period of greater than 10-15 seconds.

Flow transducer 39 continuously monitors flow into the cuff and out of the cuff. In the preferred embodiment the flow transducer 39 is a mass flow transducer which measures flow bidirectionally. The voltage output of flow transducer 39 is proportional to the magnitude and direction of flow. This output is conducted via wire 58 to integrator and comparator 40. In that circuit the flow is integrated with respect to time, so that the volume into and out of the cuff can be measured. Volume out of the cuff is then subtracted from volume into the cuff, and this difference is displayed on LED bar graph 41. In that way it can be seen by simple observation of the LED bar graph whether there is net volume into the cuff. If there is no leak in the cuff or the cuff inflation line, the LED bar graph will read zero net volume into the cuff. If there is a leak in the system, the LED bar graph will gradually indicate excess volume supplied to the cuff, which will increase continuously over time. This will indicate a cuff leak. Wire 60 connects from the output of integrator and comparator 40 to the time delay circuit 50. If a net volume enters the cuff as indicated on LED bar graph 41, time delay circuit 50 is actuated and tweeter 49 will sound, if this fault condition continues. Flow transducer 39 is chosen to have enough resolution so that net volumes of a few cc's per minute into the cuff can be detected. In this way, very early cuff leaks can be detected. Because the controller can supply up to 1-2 liters of volume per minute, cuff seal will be maintained after a cuff leak has been detected, so that an emergency situation should never occur. Only an inordinately large leak would exceed the controller's capacity to maintain cuff seal. However, this degree of leak would most likely develop over a prolonged period of time. This would allow sufficient time for the physician to reintubate the patient with a new tracheal tube 9.

The test circuit solenoids will now be described. When solenoid 35 is actuated, the pressure supply line 29 is isolated from the external cuff inflation line, allowing adjustments of both the low and high pressure controllers without affecting actual cuff pressure. When the solenoids 35 and 34 are actuated, the supply gas is routed from solenoid 35 through tube 51, through solenoid 34, into exhaust tube 30, and out exhaust port 27 to the atmosphere. This allows one to test the flow transducer 39, the integrator comparator 40, the LED bar graph 41, and leak alarm via time delay 50 and tweeter 49. When solenoid 44 is actuated, the cuff monitoring transducer 49 is connected directly to the cuff pressure supply line 29. This allows the pressure reading on pressure gauge 38 to be correlated with the pressure reading on display 46. It also allows one to test the high and low pressure alarms. In order to test the high and low pressure alarms, both solenoids 44 and 35 are actuated, in order to isolate the cuff from the controller. In order to test the high pressure alarm, solenoid 28 is actuated so that high pressure control 33 determines the system pressure. LED 47 should light immediately and tweeter 49 should sound within 10-15 seconds. Low pressure alarm is then tested by actuating solenoid 31. This has the effect of venting pressure transducer 49 and pressure gauge 38 to atmosphere through solenoid 31, out exhaust tubing 30, and out exhaust fitting 27 to atmosphere. This should have the effect of immediately lighting LED 48 and sounding tweeter 49 in 10-15 seconds.

Typical solenoid valves useable in the foregoing system are available from Precision Dynamics, Inc. of New Britain, Conn., Model No. B2215 for the two-way solenoids 28 and 34 and Model No. B3217 for the remainder which are three-way solenoid valves.

The system of the foregoing description has the advantage of offering flexible operation with automatic, bidirectional control of the cuff inflation line. The use of a low pressure PEEP type valve in series with the high pressure PEEP type valve insures that the controller is capable of adding volume to the cuff, or exhausting volume from the cuff in either respiratory phase. In addition, because the cuff line is always connected to the source gas, volume can be continuously supplied if there is a leak, irrespective of the respiratory phase. The ability to adjust the pressure point in the inspiratory tubing at which the controller switches between low and high pressure control allows one to very accurately contour the pressure curve that is applied to the cuff. The ability to accurately monitor not only peak and trough cuff pressures but the contour of the cuff pressure curve is made possible by use of a new tracheal tube which contains two separate lines into the cuff, one for inflation and one for monitoring. This monitoring is achieved by way of an instantaneous, continuous pressure display on CRT or LED bar graph. This allows both peak and trough and pressure contour control to a degree which has never been possible. Testing of this system has clearly confirmed the need for such a delicate control system since inordinately wide pressure pulses (pressure pulses of a longer duration than is necessary) and inordinately low pressure troughs previously unsuspected, have been demonstrated using this system. Both these conditions can be optimized by combining the continuous monitoring system with the adjustment of threshold, and low and high pressure control. The addition of a flow transducer in association with an integrator, comparator, and LED bar graph, an alarm circuit allows the rapid detection of cuff leaks long before any patient morbidity occurs.

The specific implementation of the system given here is only by way of illustration. Other embodiments are within the claims.

I claim:

1. Tracheal tube apparatus, comprising:
   an elongated tracheal tube having a proximal end for connection to a mechanical ventilator and a distal end for insertion into the trachea;
   an inflatable cuff bonded to and externally encircling the tracheal tube at a point close to the distal end;
   a first tubule which communicates with the interior of the cuff and which is comprised of two sections in gaseous communication, the first section of which is formed within the wall of the tracheal tube and extends from a point close to the proximal end, substantially along the length of the tracheal tube, and ends in gaseous communication with the interior of the cuff near the distal end of the tracheal tube, the second section of which is an external tubule, one end of which extends freely from the tube and the other end of which is connected to the tracheal tube at a point near the proximal end of said tracheal tube and which is in gaseous communication with the first section which is formed in the wall of the tracheal tube, said first tubule providing continuous and instantaneous monitoring of pressure conditions within said tracheal tube; and
   a second tubule which communicates with the interior of the cuff and which is comprised of two sections in gaseous communication, the first section of which is formed within the wall of the tracheal tube and extends from a point close to the proximal end, substantially along the length of the tracheal tube and ends in gaseous communication with the cuff near the distal end of the tracheal tube, the second section of which is an external tubule, one end of which extends freely from the tracheal tube and the other end of which is connected to the tracheal tube at a point near the proximal end of said tracheal tube and is in gaseous communication with the first section which is formed in the wall of the tracheal tube, said second tubule providing synchronous and rapid inflation and deflation of said tracheal cuff.

2. The tracheal tube apparatus of claim 1 in which the cross-sectional area of the second tubule is greater than that of the first tubule.

3. The tracheal tube apparatus of claim 1 in which the section of the second tubule which is formed within the wall of the tracheal tube is of an oval or crescentic shape.

4. The tracheal tube apparatus of claim 1 in which:
   the free end of the first tubule terminates in a fitting which contains a female taper which can receive a male taper from standard intravenous tubing, and a spring loaded plug which blocks flow through the fitting but which can be unseated by a male taper from standard intravenous tubing, thereby allowing free flow;
   the free end of the second tubule terminates in a fitting which contains a female taper, which contains a removable male plug, which when removed allows the female taper to receive a male taper from a standard intravenous tubing.

5. The tracheal tube apparatus of claim 1 further comprising:
   a pressure transducer in a tracheal cuff pressure controller for the purpose of continuous instantaneous monitoring and display of cuff pressure, the first tubule being connected to said pressure transducer; and the second tubule being connected to the tracheal cuff pressure controller for the purpose of cycling volume in and out of the cuff to attain specific intra-cuff pressure, as determined by the monitoring and display system connected to the first tubule so that pressures may be adjusted and synchronized with the phases of ventilation.

* * * * *

UNITED STATES PATENT AND TRADEMARK OFFICE
CERTIFICATE OF CORRECTION

PATENT NO.  : 5,235,973

DATED       : 08/17/93

INVENTOR(S) : Gary Levinson

It is certified that error appears in the above-identified patent and that said Letters Patent is hereby corrected as shown below:

In the Abstract, line 9, before "detecting pressure moni-", insert --threshold--.

Figure 3B:
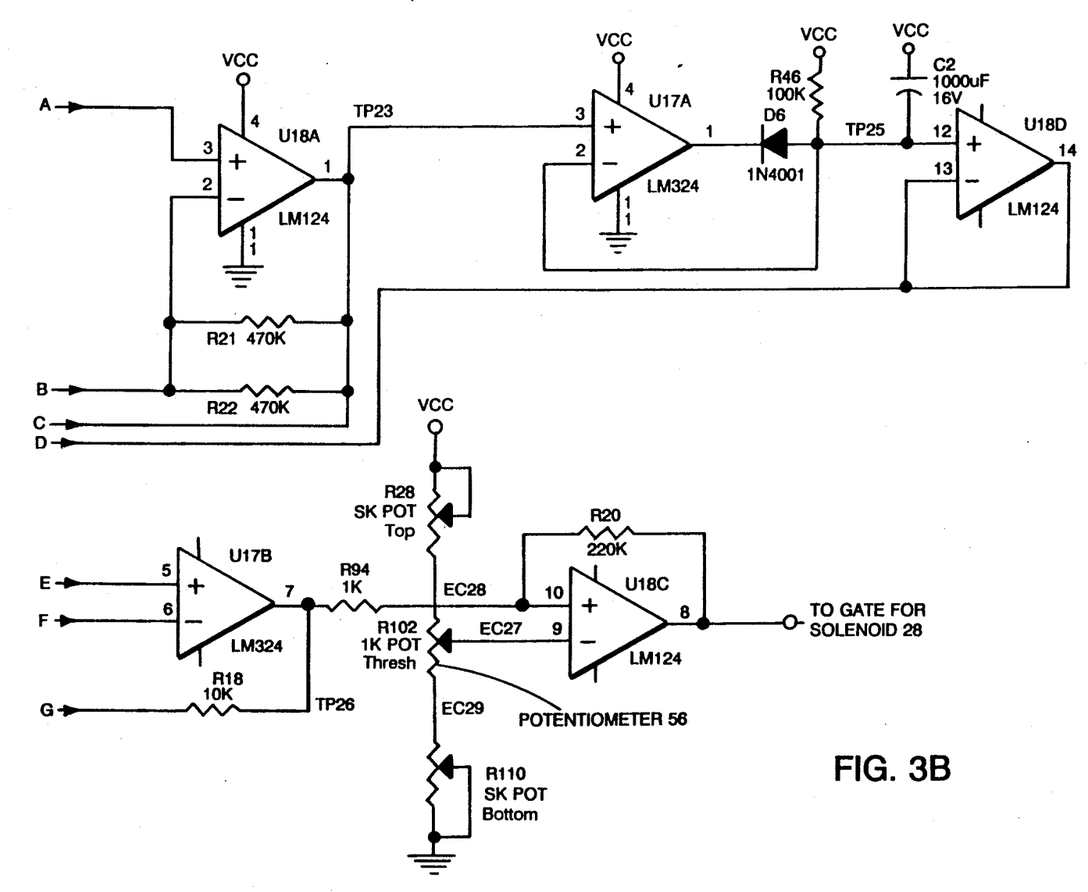

Column 4, after line 24, insert --FIG. 3A is a partial electrical schematic diagram of the threshold control circuit of FIG. 3.  FIG. 3B is the remainder of an electrical schematic diagram of the threshold control circuit of FIG. 3 which is not shown in FIG. 3A.--

Signed and Sealed this

Thirteenth Day of December, 1994

Attest:

BRUCE LEHMAN

Attesting Officer

Commissioner of Patents and Trademarks